US012625128B2

(12) United States Patent
Kimura

(10) Patent No.: US 12,625,128 B2
(45) Date of Patent: May 12, 2026

(54) SYSTEM FOR EVALUATING DISTRIBUTION OF FIBER BUNDLES IN FIBER REINFORCED MATERIAL

(71) Applicant: IHI Corporation, Tokyo (JP)

(72) Inventor: Naohiro Kimura, Tokyo (JP)

(73) Assignee: IHI Corporation, Tokyo (JP)

( * ) Notice: Subject to any disclaimer, the term of this patent is extended or adjusted under 35 U.S.C. 154(b) by 451 days.

(21) Appl. No.: 18/045,963

(22) Filed: Oct. 12, 2022

(65) Prior Publication Data

US 2023/0112177 A1     Apr. 13, 2023

Related U.S. Application Data

(63) Continuation of application No. PCT/JP2021/014487, filed on Apr. 5, 2021.

(30) Foreign Application Priority Data

Aug. 18, 2020     (JP) ................................. 2020-137884

(51) Int. Cl.
*G01N 33/36*          (2006.01)
*G01N 23/046*        (2018.01)
*G06T 7/60*            (2017.01)

(52) U.S. Cl.
CPC ......... *G01N 33/367* (2013.01); *G01N 23/046* (2013.01); *G06T 7/60* (2013.01); *G01N 2223/408* (2013.01); *G01N 2223/419* (2013.01); *G01N 2223/615* (2013.01)

(58) Field of Classification Search
CPC ............... G01N 33/367; G01N 23/046; G01N 2223/419; G01N 2223/615; G01N 2223/408; G06T 2207/10081; G06T 7/60; G06T 2207/20021; G06T 7/001
See application file for complete search history.

(56) References Cited

U.S. PATENT DOCUMENTS

2016/0349193 A1    12/2016  Guenter et al.
2017/0213357 A1     7/2017  Hishida et al.

FOREIGN PATENT DOCUMENTS

JP          11-254545  A        9/1999
JP        2008-122178  A        5/2008
JP        2009042805  A   *   2/2009    ............. G06T 15/04
(Continued)

OTHER PUBLICATIONS

Weissenbock, Johannes, et al. "Comparative visualization of orientation tensors in fiber-reinforced polymers." Proceedings of the 8th Conference on Industrial Computed Tomography (ICT 2018), Wels, Austria. 2018. (Year: 2018).*

(Continued)

*Primary Examiner* — Timothy P Graves
(74) *Attorney, Agent, or Firm* — Oblon, McClelland, Maier & Neustadt, L.L.P.

(57)                    ABSTRACT
A system for evaluating a distribution of fiber bundles in a fiber reinforced material by three-dimensional vector data of the fiber bundles is provided with: a calculator configured to divide the fiber reinforced material into a plurality of three-dimensional cells, selecting data respectively belonging to the cells, and averaging the selected data to calculate reference vector data; and a display configured to display the reference vector data two-dimensionally or three-dimensionally.

4 Claims, 5 Drawing Sheets

(56) References Cited

FOREIGN PATENT DOCUMENTS

| JP | WO 2014/080622 A1 | 5/2014 |
| JP | WO 2016/052489 A1 | 4/2016 |
| JP | 2017-507327 A | 3/2017 |
| JP | 2017-156271 A | 9/2017 |

OTHER PUBLICATIONS

International Search Report issued Jun. 22, 2021 in PCT/JP2021/014487 filed Apr. 5, 2021, citing documents 1-2 & 15-20 therein, 3 pages.
Extended European Search Report issued Aug. 26, 2024 in European Patent Application No. 21857977.9, citing reference 24 therein, 8 pages.
Weissenbock, J. et al., "Comparative Visualization of Orientation Tensors in Fiber-Reinforced Polymers", 8th Conference on Industrial Computed Tomography, vol. 23, No. 2, 2018, XP093192483, 9 pages.

* cited by examiner

SYSTEM FOR EVALUATING DISTRIBUTION OF FIBER BUNDLES IN FIBER REINFORCED MATERIAL

CROSS-REFERENCE TO RELATED APPLICATIONS

This application is a Continuation Application of PCT International Application No. PCT/JP2021/014487 (filed Apr. 5, 2021), which is in turn based upon and claims the benefit of priority from Japanese Patent Application No. 2020-137884 (filed Aug. 18, 2020), the entire contents of which are incorporated herein by reference.

BACKGROUND

Technical Field

The disclosure herein relates to a system for evaluating a distribution of fiber bundles in a fiber reinforced material.

Description of the Related Art

Various types of so-called fiber reinforced materials have been proposed, in which high-strength fibers (reinforcement fibers) are combined with matrices. Ceramic matrix fiber reinforced composites (CMCs), in which both the reinforcement fibers and the matrices are formed of ceramics, attract attention particularly for aeronautic application in light of its light-weight, heat resistance and strength.

A CMC is, in general, produced by first weaving reinforcement fibers into a fabric, and thereafter applying chemical vapor infiltration (CVI), liquid phase infiltration (particularly polymer impregnation and pyrolysis (PIP), for example), solid phase infiltration (SPI), or melt impregnation (MI) to the fabric to form a matrix of a ceramic combining the fabric. To give a three-dimensional structure to the CMC, the fabric should be in advance molded in a shape approximating to a desired final shape in parallel with the matrix formation.

Properties of the reinforced material are neither necessarily isotropic nor uniform. A distribution of the reinforcement fibers, particularly directions where the fibers run, strongly affects the properties, particularly strength, of the reinforced material. Generally, higher strength can be expected as it's closer to a direction where the reinforcement fibers run and further as the fibers are denser. It is thus desired to establish any method to evaluate a distribution of fiber bundles within a fiber reinforced material for the purpose of material assessment and pursuit of better processes.

PCT International Publications WO 2014/080622 A1 and WO 2016/052489 A1 disclose related arts.

SUMMARY

Where the fabric of the reinforcement fibers is kept flat in the fiber reinforced material, its distribution could be readily presumed because no part of the fiber bundles falls into disorder. Some problems would occur, however, when the fabric were to be molded so as to form a three-dimensional structure. Specifically, reinforcement fibers of ceramics, as being poorly stretchy, cannot stretch and contract enough to absorb deformation caused by bending the fabric and thus the fiber bundles would be unexpectedly displaced to create non-negligible disorder. As such disorder may cause the reinforcement fibers to run in unintended directions, insights about directions of the reinforcement fibers within the fiber reinforced material are extremely important.

A system according to the present disclosure is a system for evaluating a distribution of fiber bundles in a fiber reinforced material by three-dimensional vector data of the fiber bundles is provided with: a calculator configured to divide the fiber reinforced material into a plurality of three-dimensional cells, selecting data respectively belonging to the cells, and averaging the selected data to calculate reference vector data; and a display configured to display the reference vector data two-dimensionally or three-dimensionally.

Advantageous Effects

By calculating the reference vector data obtained by averaging data in each cell, it is enabled to carry out quantitative comparison among fiber reinforced materials in which fiber bundles are distinctly placed.

DESCRIPTION OF EMBODIMENTS

Exemplary embodiments will be described hereinafter with reference to the appended drawings.

In some of the drawings, reference signs "X", "Y" and "Z" mean respective axial directions in a three-dimensional coordination system. Throughout the following descriptions and appended claims, references to these directions are merely for explanatory convenience and not limiting to the embodiments. Further, the respective axial directions are not necessarily perpendicular to each other.

Figure 7:
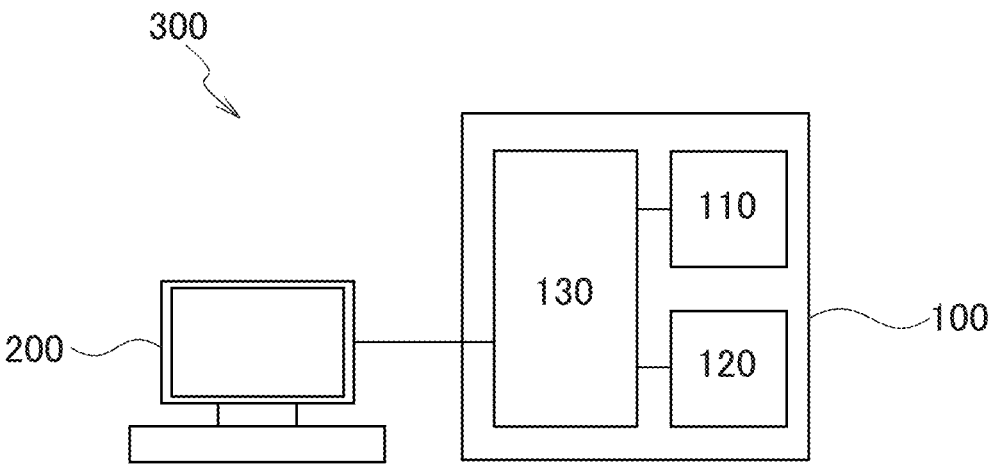
FIG. 7 is a block diagram of a system used in the disclosed evaluation technique.

The disclosure hereinafter relates to a method for evaluating a distribution of fiber bundles in a fiber reinforced material by three-dimensional vector data of the fiber bundles. This method can be partially manually but substantially automatically executed when using a system with a computer 100 and a display 200 as shown in FIG. 7. A generally available and also widely used computer 100 is applicable to the system 200 and is provided with a storage 110 such as a hard disc drive or a solid state drive, a temporary memory 120 such as a random access memory, and a computing device 130 to, by combining algorithms according to the following disclosure, execute the following processes and then express results on the display 200. The storage 110 can store not only programs 140 for executing the algorithms but also other data 150 used in computing or for comparison.

A fiber reinforced material is in general a complex in which high-strength fibers (reinforcement fibers) are combined with a matrix. The reinforcement fibers are of a ceramic such as graphite, boron nitride or silicon carbide for example. Or, they may be of a resin such as Aramid or of any proper metal or alloy. The matrix is of a thermosetting resin, a thermoplastic resin, or a proper ceramic such as silicon carbide. That formed of a matrix of a ceramic is particularly referred to as "ceramic matrix composite" (CMC).

Figure 1:
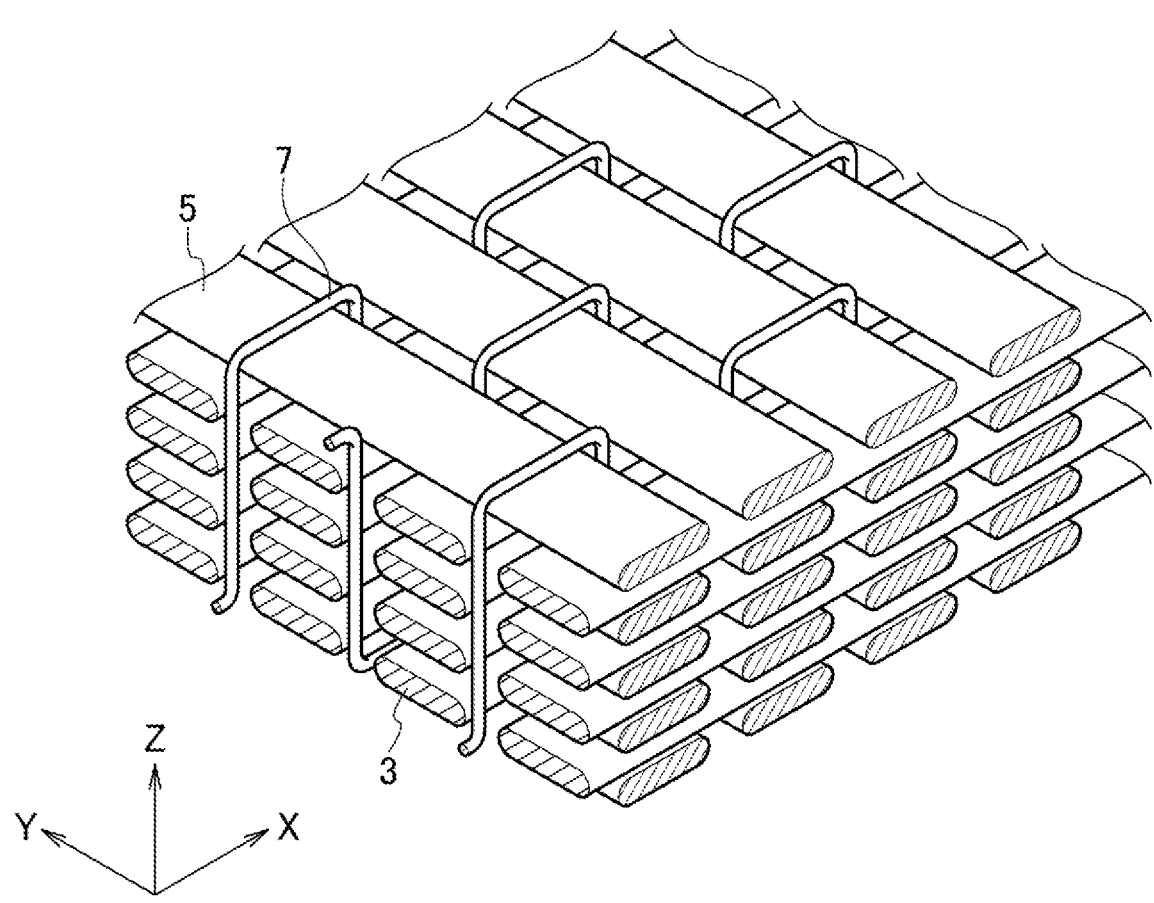
FIG. 1 is a perspective view schematically depicting a three-dimensionally formed reinforcement fiber fabric.

Referring mainly to FIG. 1, to the fiber reinforced material according to the present embodiment applicable is a three-dimensional reinforcement fiber fabric in which reinforcement fibers are woven into a three-dimensional structure for example. In the three-dimensional reinforcement fiber fabric, the fibers run not only in the X- and Y-directions but also in the Z-direction and loosely bind each other. According to one example, fiber bundles 3, 5 run in the X-, Y-directions respectively and are mutually layered, and fiber bundles 7 running in the Z-direction combine them together, thereby forming a three-dimensional reinforcement fiber fabric. This is of course no more than an example. These fibers may be not rendered perpendicular to each other but may be obliquely woven, or the fabric may be a two-dimensional fabric, in which the fibers are not layered in the thickness direction.

Figure 2:
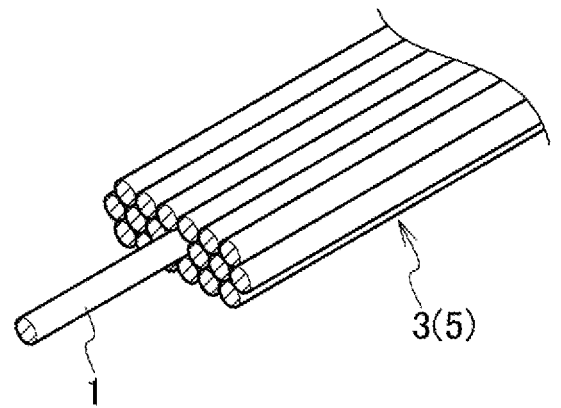
FIG. 2 is a perspective view schematically depicting a reinforcement fiber bundle.

Referring to FIG. 2, the fiber bundles 3, 5, 7 are respectively those in which plural reinforcement fibers 1 running substantially in parallel are bundled together. Or, each fiber bundle 7 among them may be a single fiber. In the drawn example, the reinforcement fibers 1 are illustrated to be straight but may be twisted together. One fiber bundle 3, 5, 7 includes from 500 to 800 reinforcement fibers 1 bundled together, while the number may be arbitrarily increased or decreased.

The reinforcement fiber fabric is molded into a proper shape by any known molding method such as press-forming or bagging. This is followed by, or in parallel, infiltrating a matrix precursor therein and curing them to form the matrix, thereby producing the fiber reinforced material. A product 10 illustrated in FIG. 3, which is formed of the fiber reinforced material, is a stator vane to constitute a turbine nozzle of a gas turbine engine. This is of course for explanatory convenience, and therefore various products can be produced from the fiber reinforced material.

In the turbine stator vane, a vane section 11 forms a so-called airfoil shape to express a curvature, and an outer band section 13 and an inner band section 15 are, approximately at a right angle, bent from the vane section 11. The outer band section 13 and the inner band section 15 respectively have further bent sections. Needless to say, the fabric embedded in the turbine stator vane is deformed to follow such an outline and, as discussed above, the reinforcement fiber bundles are displaced so as to enable such deformation. Therefore, even though the reinforcement fiber bundles in the original fabric were arranged orderly, the distribution and the directions of the reinforcement fiber bundles after molding would be non-uniform and uneven.

Figure 3:
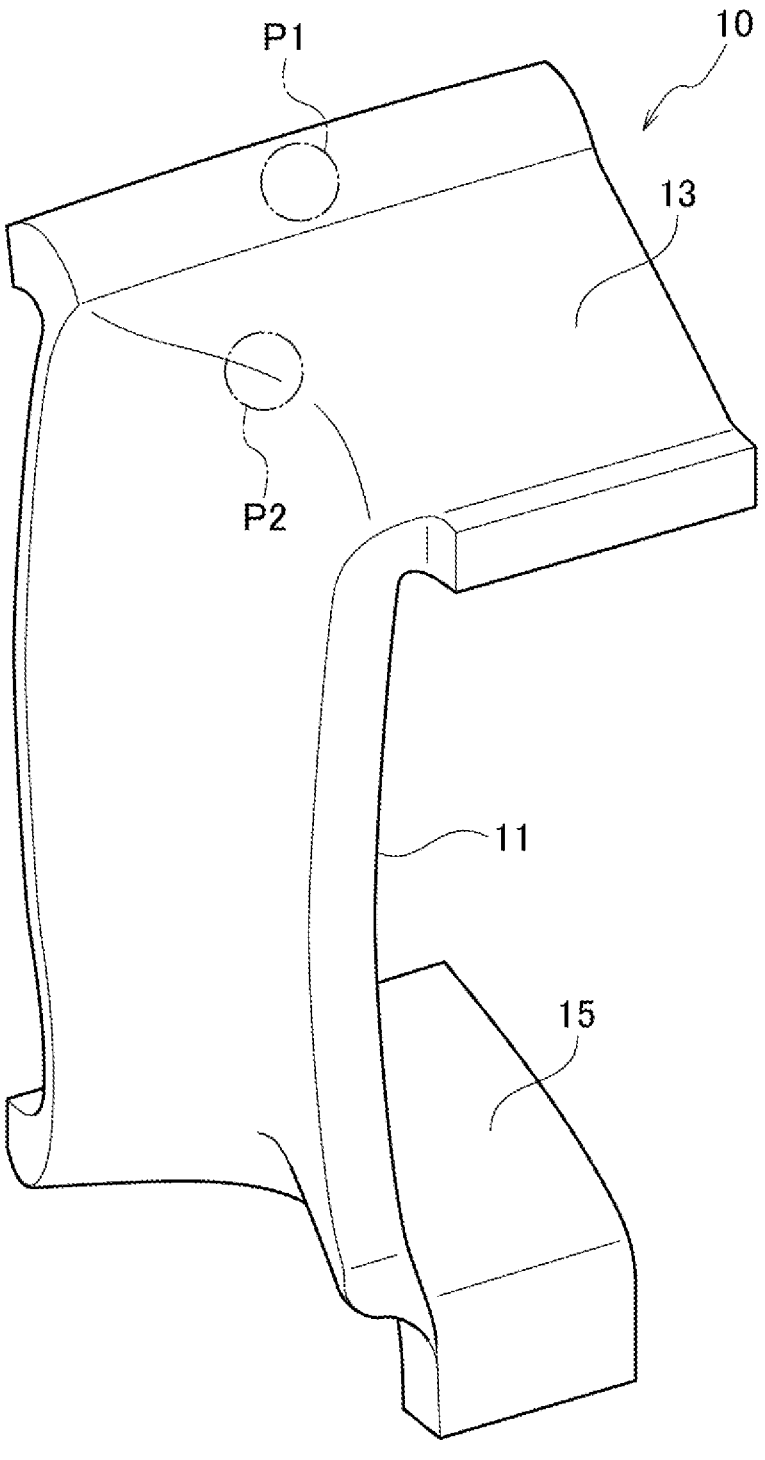
FIG. 3 is a perspective view of a schematic member of a fiber reinforced material.
Figure 4:
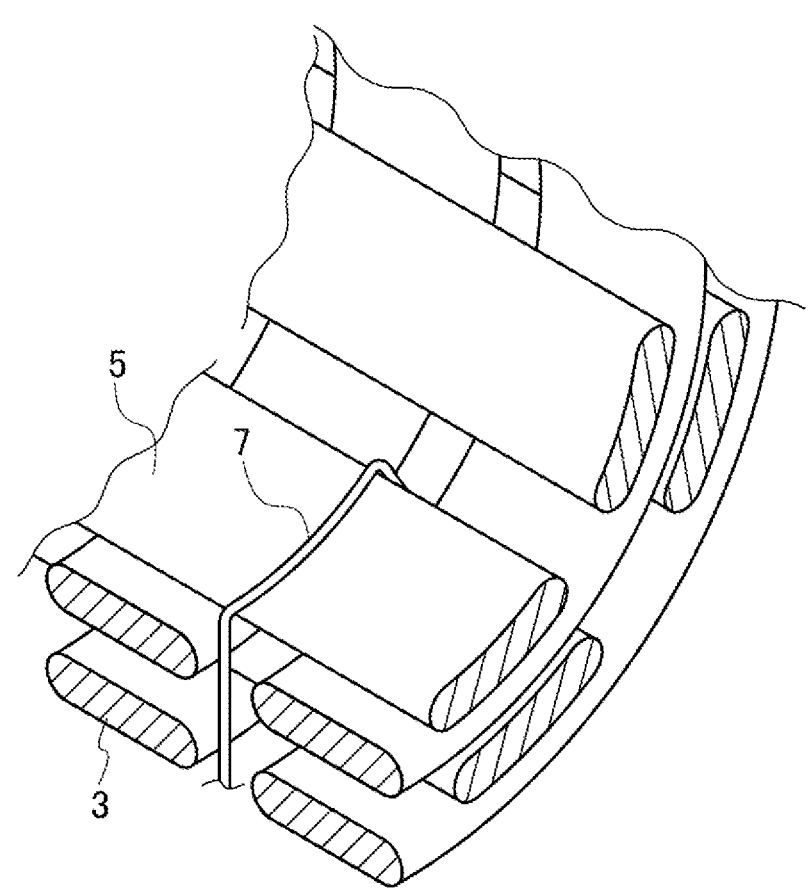
FIG. 4 is a perspective view schematically depicting a fabric at a simply bent part.

At a portion to which a sign P1 is attached in FIG. 3 for example, as the fabric is merely given a simple curve that is approximately perpendicular to the fiber bundles, as illustrated in FIG. 4, the fiber bundles could respectively warp along the curve and therein displace only slightly relative to each other. The displacement of the fiber bundles in this portion is not noticeable.

Figure 5:
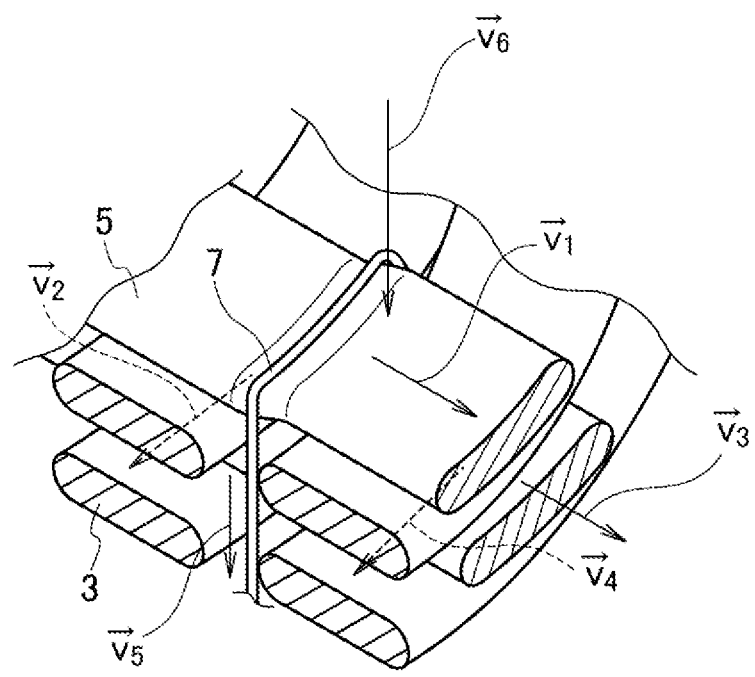
FIG. 5 is a perspective view schematically depicting a fabric at a complicatedly bent part and three-dimensional vectors along its respective fiber bundles.

At any complicatedly bent portion, like a portion to which a sign P2 is attached in FIG. 3, where the fabric is required to curve in various directions and the curvature is necessarily steep, the fiber bundles are required not only to warp individually but also to be displaced relative to each other because otherwise they cannot absorb induced deformation. In the example shown in FIG. 5, the fiber bundles 3 must change mutual spaces and thus lose parallelism. Further, the relative height between neighboring fiber bundles 3 becomes uneven and, as reflecting it, the fiber bundles 5 crossing them undulate in the Z-axis direction.

In assessing properties of a fiber reinforced material, it is important to gain insights about the distribution of the fiber bundles inside, particularly directions where they run, and greater importance would be attached in regard to portions like the complicatedly bent portion with the sign P2.

The distribution and the directions of the fiber bundles in the fiber reinforced material can be three-dimensionally observed by using any proper interior observation means. X-ray computerized tomography (X-ray CT) is applicable even to an optically opaque substance such as CMC for example. Or, in a case of a fiber reinforced material with a transparent resin, optical means are possibly applied. Of course in place of or in addition to these means, any interior observation means using any other particles could be used.

Obtained three-dimensional observation results can be generally subject to any qualitative analysis but are barely adapted to quantitative analysis. It is, however, possible to extract vector data about the fiber bundles by applying proper publicly-known image analysis means. These obtained vector data are used in this embodiment. While FIG. 5 selectively shows some of included fiber bundles, vectors respectively parallel to these bundles are schematically attached to the drawing. The extracted data are a set of such vectors.

The extracted vector data are a set of a very large number of data and are, unless processed, inconvenient for comparison with any standard that is calculated or supposed in any way for example. Thus in the present embodiment, the extracted vector data set is processed in a way as described below and converted into a data set comparable with another data set. Such processing is, as described above, executable by a combination of algorithms and a widely used computer in accordance with the disclosure as described below.

Figure 6:
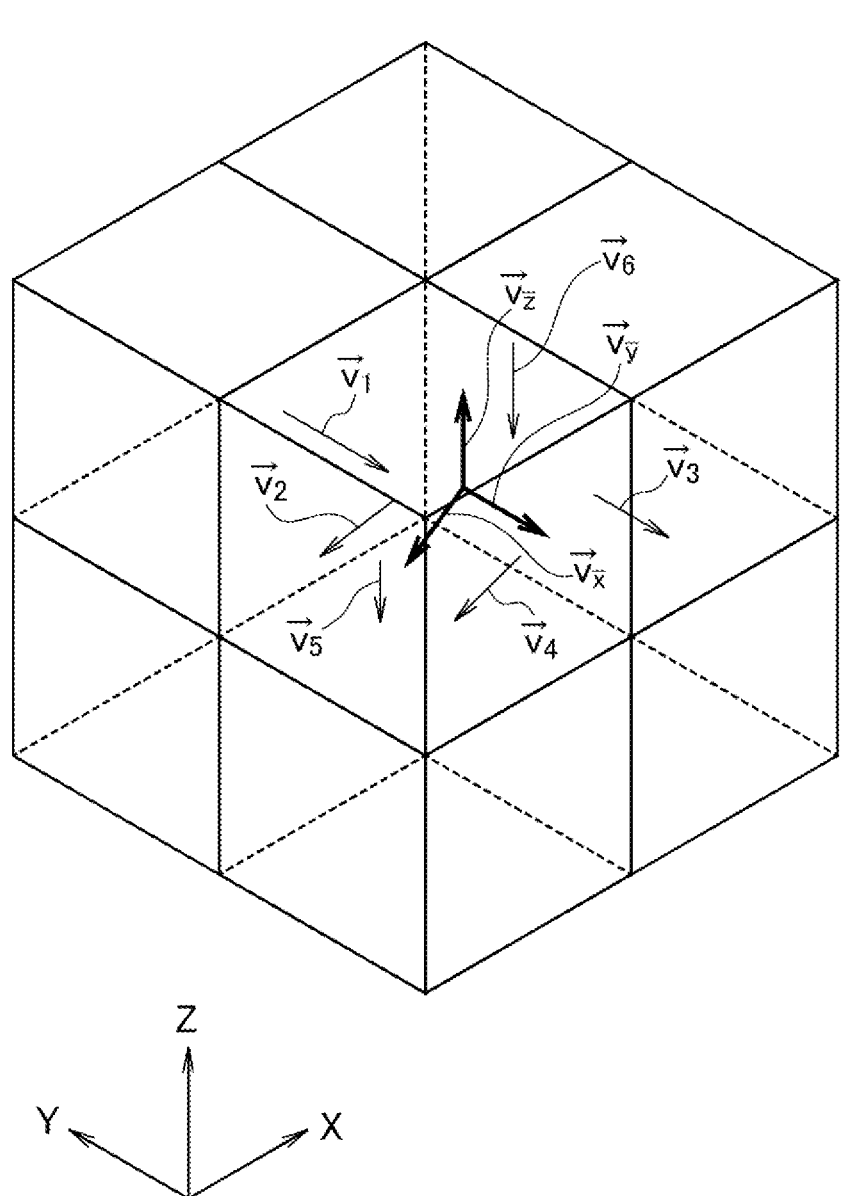
FIG. 6 is a perspective view schematically depicting three-dimensional cells and three-dimensional vectors belonging to one of the cells.
Figure 8:
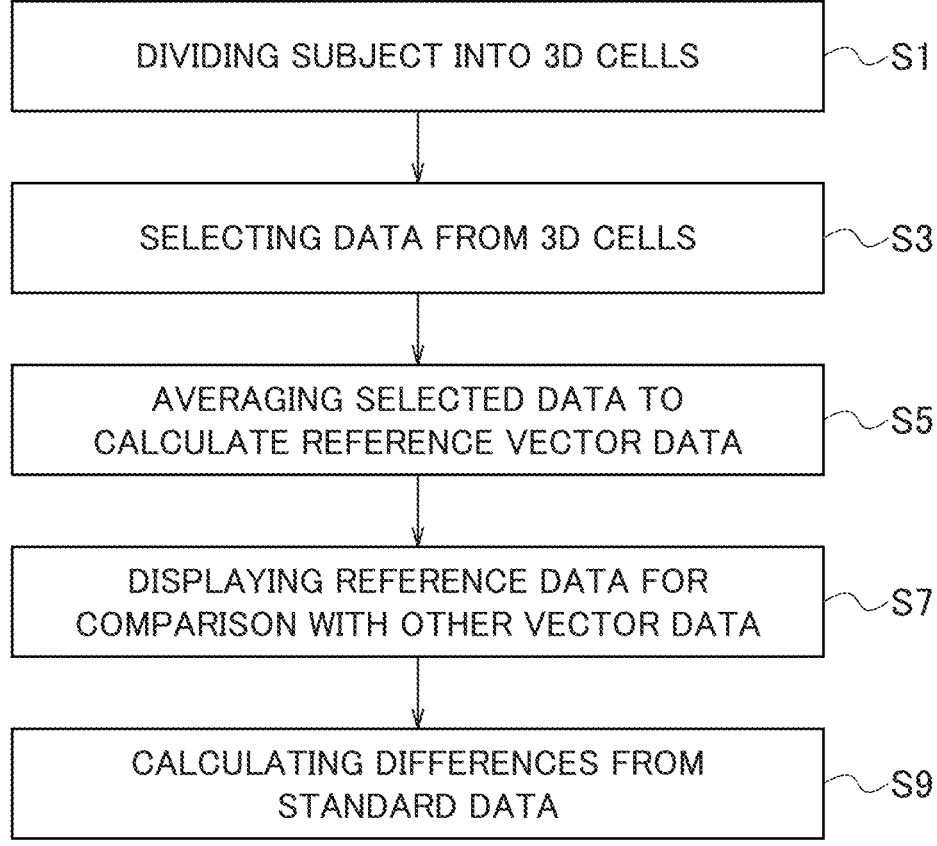
FIG. 8 is a flowchart representing a process executed by the system.

Referring to FIGS. 6 and 8, the process includes: dividing the totality of the fiber reinforced material in question or any space including a region at issue in the material into proper three-dimensional lattices to set out a plurality of three-dimensional cells (step S1). Although FIG. 6 merely shows a small number of vectors in a particular cell, actually a large number of vectors respectively belong to all the cells. From the extracted vector data, data belonging to each cell are sorted out on the basis of coordinates of respective start and end points (step S3) and are averaged in each cell (step S5).

$$\vec{V} = \frac{\sum \vec{v}}{n} \tag{1}$$

$$\vec{V} = \frac{\sum \vec{v}}{n} \bigg/ \left| \frac{\sum \vec{v}}{n} \right| \tag{2}$$

Simple arithmetic averages could be taken in accordance with the equation (1) or these averages could be further normalized in accordance with the equation (2). Or alternatively, each vector could be properly weighted and then weighted averages could be taken. Calculated results will be referred to as "reference vector data" in the following description and the appended claims.

In a case where it is determinable which of the extracted data derives from which of fibers (or fiber bundles) and where the determined fiber is directed in the fabric, on the basis of the information, averages could be taken respectively by vectors related to fibers (or fiber bundles) directed in a particular direction in the fabric before deforming. FIG. 6 shows average vectors after deforming respectively averaged with respect to the X-, Y- and Z-directions. The average vectors are calculated on the basis of the equation (3).

$$\begin{aligned} \vec{v_x} &= \text{average}\left(\vec{v}_2, \vec{v}_4\right) \\ \vec{v_y} &= \text{average}\left(\vec{v}_1, \vec{v}_3\right) \\ \vec{v_z} &= \text{average}\left(\vec{v}_5, \vec{v}_6\right) \end{aligned} \qquad (3)$$

As will be understood from FIG. 3, a fabric inherently contains many fiber bundles in various positions and in various directions. Further as will be understood from FIG. 4, as the fabric is deformed, these fiber bundles are displaced and also change these directions. Therefore to compare one set of data obtained from one fiber reinforced material with another set of data obtained from another fiber reinforced material is unlikely to give meaningful insights. Because the reference vector data obtained in the present embodiment are representative of directions of fiber bundles in each cell, they are comparable to standard data obtained from similar lattices.

The reference vector data may be, as they are for example, displayed two-dimensionally or three-dimensionally on a display (step S7). Unlike raw interior observation results or vector data, the picture on the display enables observation on vectors representative of each cell, and thereby gives considerable insights. For example, it is possible to visually compare it with a stress distribution obtained in numerical calculations or with reference vector data obtained in another opportunity. If the directions of stress in any portion are aligned with the directions of the fiber bundles, it could be expected that this portion is relatively tough. If some misfits exist, the portion is expected to be relatively weak.

For better quantitative comparison, the reference vector data may be further subject to any calculation process, which for example includes: getting differences from the standard data (step S9). If reference vector data obtained in another opportunity are adopted as the standard data, the differences represent variations in directions of fiber bundles from one production chance to another and three-dimensional display thereof facilitates understanding as to which regions are likely to create such variations. Of course any standard data are arbitrarily selected and, instead of difference calculation, any available calculation may be used.

Although certain embodiments have been described above, modifications and variations of the embodiments described above will occur to those skilled in the art, in light of the above teachings.

INDUSTRIAL APPLICABILITY

By calculating the reference vector data obtained by averaging data in each cell, the disclosure enables quantitative comparison among fiber reinforced materials in which fiber bundles are distinctly placed.

What is claimed is:

1. A system for evaluating a distribution of fiber bundles in a fiber reinforced material by three-dimensional vector data of the fiber bundles, comprising:
   a calculator configured to divide a space including a region of the fiber reinforced material into a plurality of three-dimensional cells, select data respectively belonging to the cells, and average the selected data to calculate reference vector data, the data belonging to each cell being sorted out based on coordinates of respective start and end points of respective vectors and are averaged in each cell; and
   a display configured to display the reference vector data two-dimensionally or three-dimensionally.

2. The system of claim 1, further comprising:
   a comparator configured to compare the reference vector data with other vector data.

3. The system of claim 2, wherein the comparator comprises a delta display configured to calculate differences between the reference vector data and the other vector data and convert the differences into differences in hue to make the display display the differences in hue.

4. The system of claim 1, wherein the reference vector data are representative of directions of fiber bundles in each cell.

* * * * *